United States Patent
Afzal et al.

(10) Patent No.: US 6,503,450 B1
(45) Date of Patent: *Jan. 7, 2003

(54) INTEGRATED BLOOD OXYGENATOR AND PUMP SYSTEM

(75) Inventors: Thomas A. Afzal, Menlo Park, CA (US); Jean-Pierre Dueri, Sunnyvale, CA (US); Alex Leynov, Walnut Creek, CA (US); Anthony Makarewicz, Dublin, CA (US); Alec A. Piplani, Mountain View, CA (US); Greg Potts, Mountain View, CA (US)

(73) Assignee: Cardiovention, Inc., Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/475,467

(22) Filed: Dec. 30, 1999

Related U.S. Application Data

(63) Continuation-in-part of application No. 09/430,219, filed on Oct. 29, 1999, now Pat. No. 6,428,747, which is a continuation-in-part of application No. 09/223,676, filed on Dec. 30, 1998, now Pat. No. 6,379,618.

(51) Int. Cl.$^7$ .................... A61M 1/14; A61M 37/00
(52) U.S. Cl. .................... 422/45; 422/48; 604/4.01; 604/6.11; 604/6.13; 604/6.14; 96/257
(58) Field of Search .................... 604/4.01, 6.01, 604/6.09, 6.11, 6.13–6.14; 422/44–48; 210/780–82, 222–23, 150–51, 174–84, 186, 194, 322, 257, 295, 321.72–321.81, 321.84–321.87, 323.1, 348.51, 383, 407, 416.1, 433.1, 418, 483, 497.01, 497.1–497.3, 499, 512, 542, 321.9, 500.23, 456; 96/4, 6–11, 234–40, 243, 257–60, 268, 281, 290, 299, 322–25, 355–56, 374, 358–61, 269, 267, 303.05, 357.61

(56) References Cited

U.S. PATENT DOCUMENTS

| 3,026,871 A | 3/1962 | Thomas | 128/214 |
|---|---|---|---|
| 3,204,631 A | 9/1965 | Fields | 128/214 |
| 3,466,148 A | 9/1969 | Everett | 23/258.5 |
| 3,468,631 A | 9/1969 | Raible et al. | 23/258.5 |
| 3,674,440 A | 7/1972 | Kitrilakis | 23/258.5 |
| 3,768,977 A | 10/1973 | Brumfield et al. | 23/258.5 |
| 3,794,468 A | 2/1974 | Leonard | 23/258.5 |

(List continued on next page.)

FOREIGN PATENT DOCUMENTS

| AU | 564831 | 8/1987 | A61M/1/00 |
|---|---|---|---|
| EP | 0 599 138 A2 | 1/1994 | A61M/1/10 |
| GB | 1 437 493 | 9/1973 | A61M/1/03 |

OTHER PUBLICATIONS

Berman, J. et al., "Oxygen Transfer to Water or Blood Flowing in a Rotating Straight Tube," Biomedical Engineering Center, Northwestern University, 4 pgs.

Berman, J. et al., "Transport in Rotating Tubular Oxygenators," Biomedical Engineering Center, Northwestern University, 4 pgs.

(List continued on next page.)

Primary Examiner—Angela D. Sykes
Assistant Examiner—P M Bianco
(74) Attorney, Agent, or Firm—Fish & Neave; Nicola A. Pisano

(57) ABSTRACT

Improvements to integrated blood pump/oxygenator having a rotating hollow fiber bundle assembly that both oxygenates and pumps blood are provided. An inner member arranged along a central axis of the device accelerates blood entering the fiber bundle to reduce microbubble generation and blood trauma. Shearing loads imposed on the fiber elements of the fiber bundle are reduced by the addition of a reinforcement structure, while the gas flow path is configured to reduce flooding and loss of oxygenation efficiency due to occasional rupture of fiber elements.

42 Claims, 8 Drawing Sheets

U.S. PATENT DOCUMENTS

| | | | |
|---|---|---|---|
| 3,841,837 A | 10/1974 | Kitrilakis et al. | 23/258.5 |
| 3,970,408 A | 7/1976 | Rafferty et al. | 415/60 |
| 3,998,593 A | 12/1976 | Yoshida et al. | 23/258.5 |
| 4,075,091 A | 2/1978 | Bellhouse | 210/19 |
| 4,376,095 A | 3/1983 | Hasegawa | 422/46 |
| 4,400,275 A | 8/1983 | Ramshaw et al. | 210/321.1 |
| 4,490,331 A | 12/1984 | Steg, Jr. | 422/46 |
| 4,558,996 A | 12/1985 | Becker et al. | 417/374 |
| 4,620,965 A | 11/1986 | Fukusawa et al. | 422/46 |
| 4,639,353 A | 1/1987 | Takemura et al. | 422/46 |
| 4,698,207 A | 10/1987 | Bringham et al. | 422/46 |
| 4,791,054 A | 12/1988 | Hamada et al. | 435/2 |
| 4,808,378 A | 2/1989 | Nakanishi et al. | 422/48 |
| 4,944,748 A | 7/1990 | Bramm et al. | 623/3 |
| 4,975,247 A | 12/1990 | Badolato et al. | 422/48 |
| 5,049,134 A | 9/1991 | Golding et al. | 604/151 |
| 5,120,302 A * | 6/1992 | Vescovini et al. | |
| 5,162,101 A | 11/1992 | Cosentino et al. | 422/46 |
| 5,217,689 A | 6/1993 | Raible | 422/46 |
| 5,230,862 A | 7/1993 | Berry et al. | 422/48 |
| 5,263,924 A | 11/1993 | Mathewson | 604/4 |
| 5,266,265 A | 11/1993 | Raible | 422/46 |
| 5,270,005 A | 12/1993 | Raible | 422/46 |
| 5,271,743 A | 12/1993 | Hattler | 604/26 |
| 5,308,314 A | 5/1994 | Fukui et al. | 604/4 |
| 5,308,320 A | 5/1994 | Safer et al. | 604/4 |
| 5,312,589 A | 5/1994 | Reeder et al. | 422/45 |
| 5,391,142 A | 2/1995 | Sites et al. | 604/4 |
| 5,399,074 A | 3/1995 | Nose et al. | 417/423.1 |
| 5,411,706 A | 5/1995 | Hubbard et al. | 422/46 |
| 5,575,630 A | 11/1996 | Nakazawa et al. | 417/420 |
| 5,591,404 A | 1/1997 | Mathewson | 422/48 |
| 5,601,418 A | 2/1997 | Ohara et al. | 417/420 |
| 5,626,759 A | 5/1997 | Krantz et al. | 210/645 |
| 5,626,825 A | 5/1997 | Novello et al. | 422/45 |
| 5,643,794 A | 7/1997 | Liu et al. | 435/289.1 |
| 5,728,069 A | 3/1998 | Montevecchi et al. | 604/151 |
| 5,770,149 A * | 6/1998 | Raible | |
| 5,830,370 A * | 11/1998 | Maloney et al. | 210/321.63 |
| 5,900,142 A | 5/1999 | Maloney, Jr. et al. | 210/179 |
| 6,106,776 A * | 8/2000 | Borovetz et al. | |
| 6,217,826 B1 * | 4/2001 | Reeder et al. | |
| 6,224,829 B1 * | 5/2001 | Piplani et al. | |

OTHER PUBLICATIONS

Berman, J. et al., "Mass Transfer to Fluids Flowing Through Rotating Nonaligned Straight Tubes," *Journal of Biomedical Engineering*, R. Skalak et al., eds., The American Society of Mechanical Engineers, 1986, pp. 342–349.

Gaylor, J.D.S. et al., "Gas Transfer and Thrombogenesis in an Annular Membrane Oxygenator with Active Blood Mixing," *Transactions: American Society for Artificial Internal Organs, vol. XIX*, G.E. Schreiner et al., eds., Georgetown University Printing Department, 1973, pp. 516–524.

Gaylor, J.D.S. et al., "The Taylor–Vortex membrane oxygenator: design analysis based on a predictive correlation for oxygen transfer," *Physiological and Clinical Aspects of Oxygenator Design*, S.G. Dawids & H.C. Engell, eds., Elsevier Scientific Publishing Co., 1976, pp. 65–76.

Illickal, M.M. et al., "Boundary Layer Phenomenon in Membrane Oxygenators," *Surgical Forum*, H.W. Scott et al., eds., American College of Surgeons, 1968, pp. 134–136.

Kitrilakis, S. et al., "A Rotating Disk Membrane Oxygenator," *Artificial Lungs for Acute Respiratory Failure, Theory and Practice*, W. Zapol and J. Qvist eds., Academic Press, 211–221 (1976).

Lewis, F.R. et al., "A Combined Membrane Pump–Oxygenator: Design and Testing," *Transactions: American Society for Artificial Internal Organs, vol. XX–A*, G.E. Schreiner et al., eds., Georgetown University Printing Department, 1974, pp. 253–261.

Makarewicz, A.J. et al., "A Pumping Intravascular Artificial Lung with Active Mixing," *ASAIO Journal*, 39(3):M466–M469 (1993).

Makarewicz, A.J. et al., "A Pumping Artificial Lung," *ASAIO Journal*, 40(3):M518–M521 (1994).

Makarewicz, A.J. et al., "New Design for a Pumping Artificial Lung," *ASAIO Journal*, 42(5):M615–M619 (1996).

Mottaghy, K. et al., "Effect of Combined Shear, Secondary and Axial Flow of Blood on Oxygen Uptake," *Chem. Eng. Commun.: vol. 36*, Gordon and Breach Science Publishers, 1985, pp. 269–279.

Ratan, Ram S. et al., "Experimental evaluation of a rotating membrane oxygenator," *The Journal of Thoracic and Cardiovascular Surgery: vol. 53, No. 4*, B. Blades, ed., The C.V. Mosby Co., 1967, pp. 519–526.

Sakakibara, Shigeru et al., "The Centrifugal Oxygenator: Clinical Experience in 1,215 Patients," *The Annals of Thoracic Surgery: vol. 6, No. 5*, 1968, pp. 443–449.

Smeby, L.C., "The Taylor–Vortex Membrane Oxygenator," *Artificial Organs*, R.M. Kenedi et al., eds., University Park Press, 1977, pp. 70–82.

Subramanian, V.A. et al., "Comparative Evaluation of a New Disposable Rotating Membrane Oxygenator with Bubble Oxygenator," *The Annals of Thoracic Surgery: vol. 21*, No. 1, Little, Brown and Co., 1976, pp. 48–54.

* cited by examiner

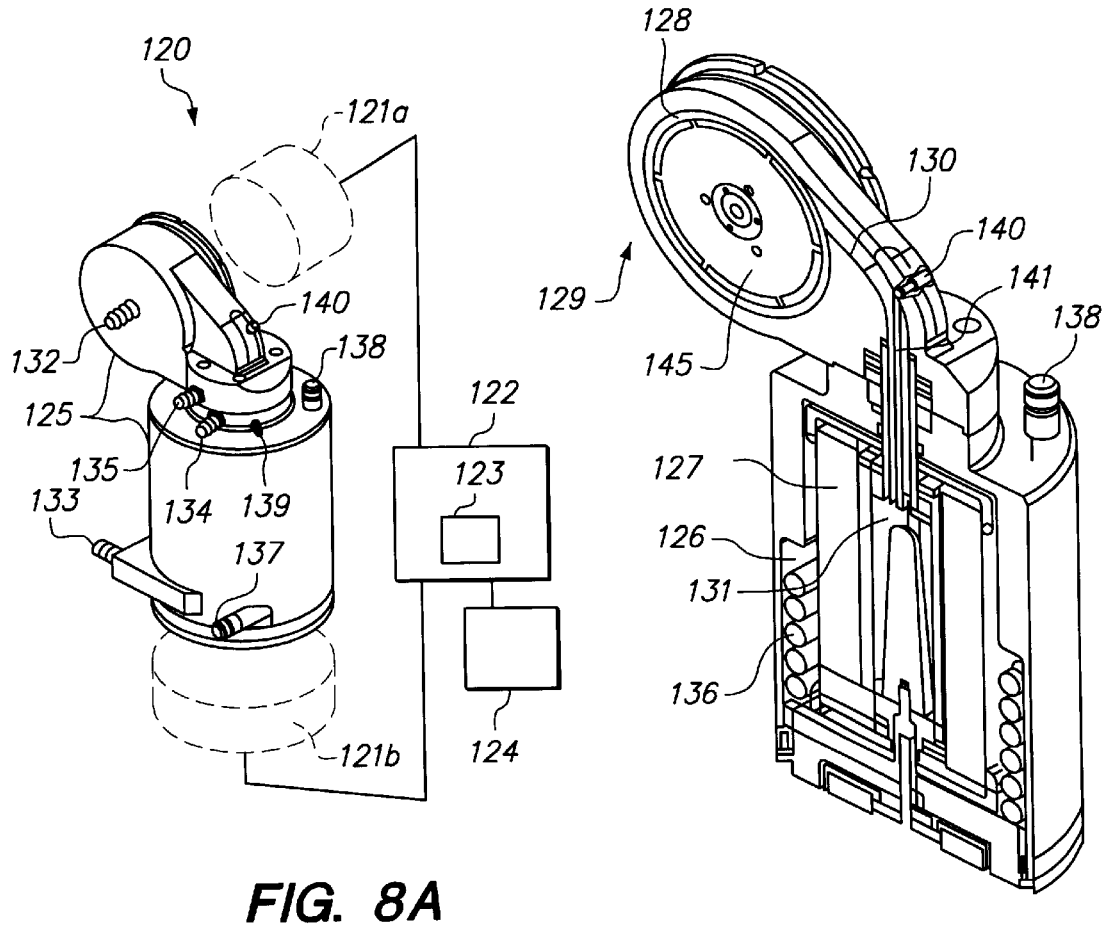
FIG. 8A
FIG. 8B
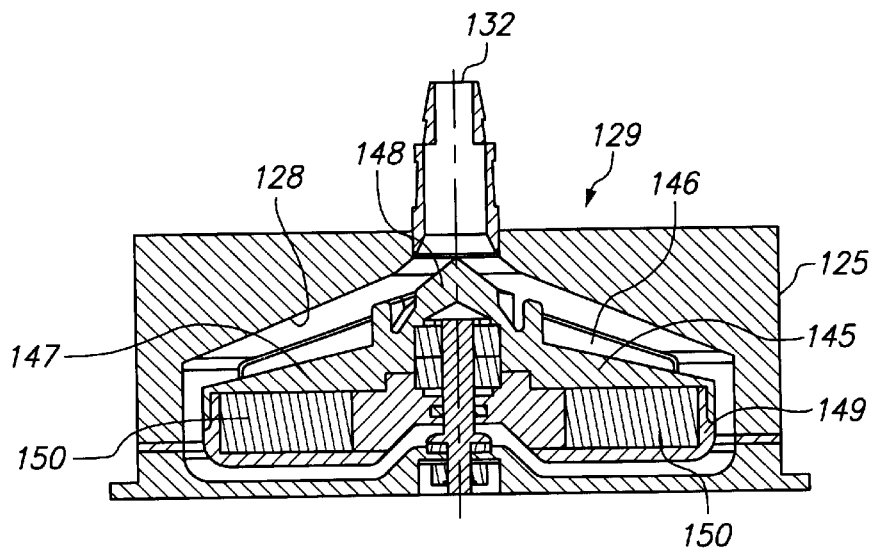
FIG. 9

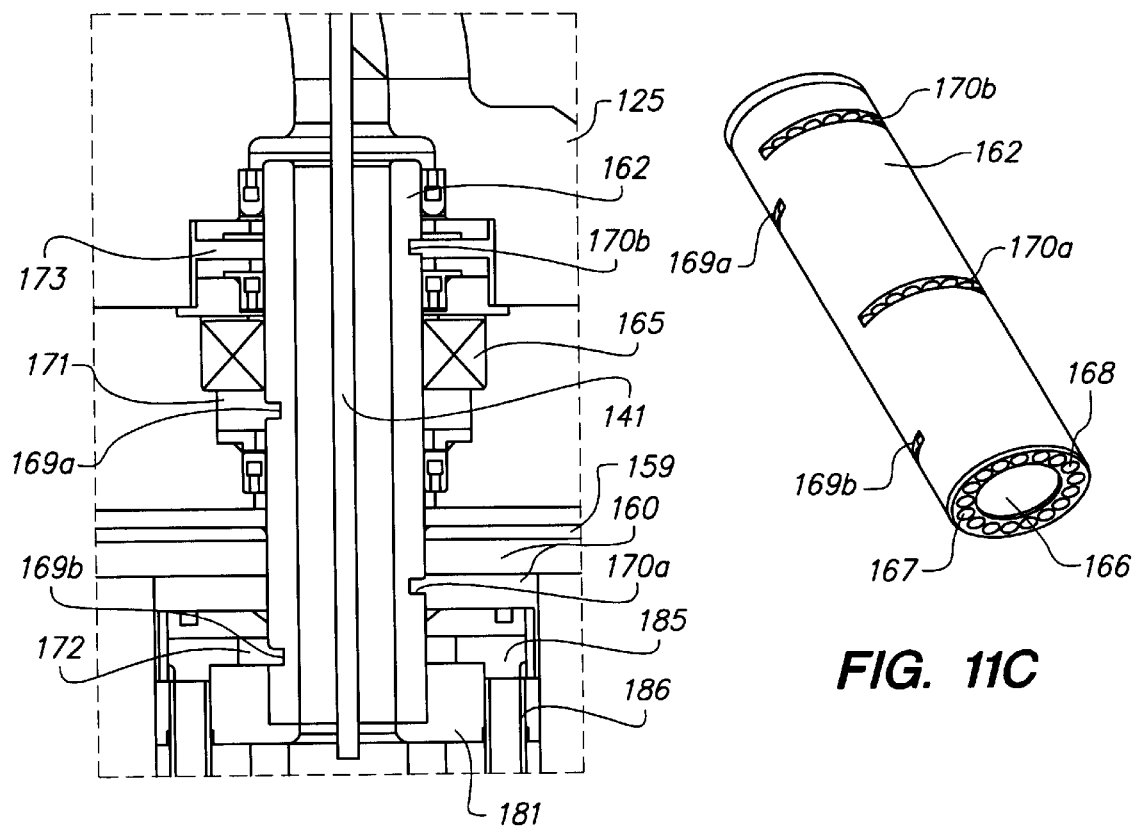
FIG. 11A
FIG. 11C
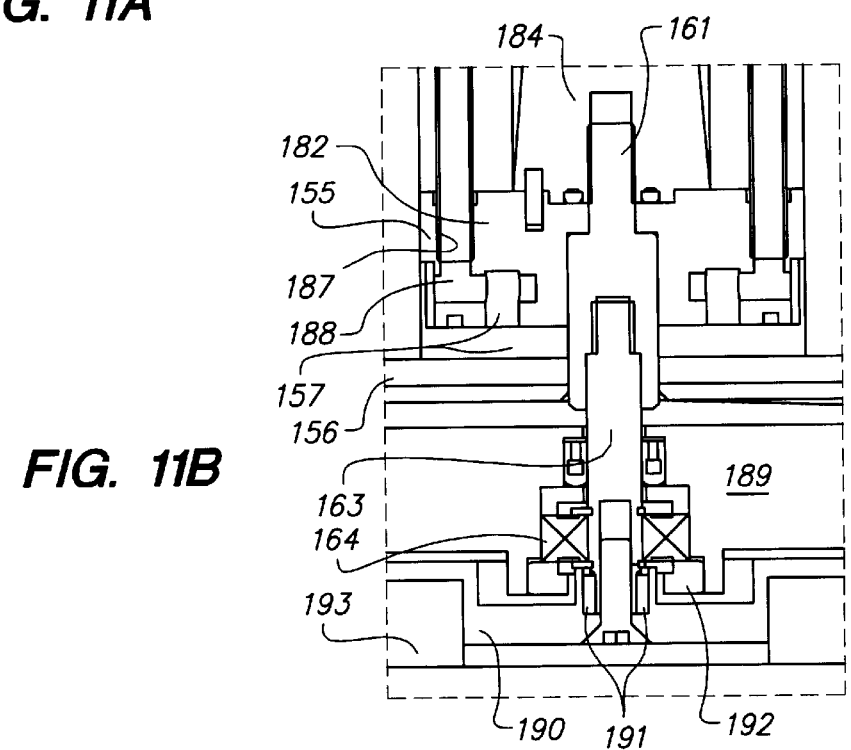
FIG. 11B

INTEGRATED BLOOD OXYGENATOR AND PUMP SYSTEM

REFERENCE TO RELATED APPLICATIONS

This application is a continuation-in-part of U.S. patent application Ser. No. 09/430,219, filed Oct. 29, 1999 now U.S. Pat. No. 6,428,747, which is a continuation-in-part of U.S. patent application Ser. No. 09/223,676, filed Dec. 30, 1998, now U.S. Pat. No. 6,379,618.

FIELD OF THE INVENTION

The present invention relates to extracorporeal systems for oxygenating and pumping blood during cardiac surgery. More specifically, the present invention relates to an integrated oxygenator and pump system wherein the gas diffusion fibers form a pumping element.

BACKGROUND OF THE INVENTION

Each year hundreds of thousands of people are afflicted with vascular diseases, such as arteriosclerosis, that result in cardiac ischemia. For more than thirty years, such disease, especially of the coronary arteries, has been treated using open surgical procedures, such as coronary artery bypass grafting. During such bypass grafting procedures, a sternotomy is performed to gain access to the pericardial sac, the patient is put on cardiopulmonary bypass, and the heart is stopped using a cardioplegia solution.

Recently, the development of minimally invasive techniques for cardiac bypass grafting, for example, by Heartport, Inc., Redwood City, Calif., and CardioThoracic Systems, Inc., Menlo Park, Calif., have placed a premium on reducing the size of equipment employed in the sterile field. Whereas open surgical techniques typically provide a relatively large surgical site that the surgeon views directly, minimally invasive techniques require the placement of endoscopes, video monitors, and various positioning systems for the instruments. These devices crowd the sterile field and can limit the surgeon's ability to maneuver.

At the same time, however, the need to reduce priming volume of the oxygenator and pump, and the desire to reduce blood contact with non-native surfaces has increased interest in locating the oxygenator and pump as near as possible to the patient.

In recognition of the foregoing issues, some previously known cardiopulmonary systems have attempted to miniaturize and integrate certain components of cardiopulmonary systems. U.S. Pat. Nos. 5,266,265 and 5,270,005, both to Raible, describe an extracorporeal blood oxygenation system having an integrated blood reservoir, an oxygenator formed from a static array of hollow fibers, a heat exchanger, a pump and a pump motor that is controlled by cable connected to a control console.

The systems described in the foregoing patents employ relatively short flow paths that may lead to inadequate gas exchange, due to the development of laminar flow zones adjacent to the hollow fibers. U.S. Pat. No. 5,411,706 to Hubbard et al. describes one solution providing a longer flow path by recirculating blood through the fiber bundle at a higher flow rate than the rate at which blood is delivered to the patient. U.S. Pat. No. 3,674,440 to Kitrilakis and U.S. Pat. No. 3,841,837 to Kitrilakis et al. describe oxygenators wherein the gas transfer surfaces form an active element that stirs the blood to prevent the buildup of boundary layers around the gas transfer surfaces.

Makarewicz et al., "A Pumping Intravascular Artificial Lung with Active Mixing," *ASAIO Journal*, 39(3) :M466–M469 (1993), describes an intravascular device having a gas exchange surface made of microporous fibers formed into an elongated helical vane. The elongated helical vane permits not only gas exchange, but also may be rotated to pump blood through the device.

Makarewicz et al., "A Pumping Artificial Lung," *ASAIO Journal*, 40(3):M518–M521 (1994) describes an adaptation of the foregoing device in which the microporous fiber bundles were formed into multi-lobed clover-leaf vanes potted along a central axis. The vanes were substituted for the vanes of a BIOMEDICUS® blood pump (a registered trademark of Bio-Medicus, Eden Prairie, Minn.). The authors concluded that while the concept of achieving simultaneous pumping and oxygenation appeared feasible, additional design and testing would be required, and problems, such as hemolysis and platelet activation, must be addressed.

Makarewicz et al., "New Design for a Pumping Artificial Lung," *ASAIO Journal*, 42(5):M615–M619 (1996), describes an integrated pump/oxygenator in which a hollow fiber bundle replaces the multi-lobed vanes of the above-described design. The hollow fiber bundle is potted to an inlet gas manifold at the bottom, and an outlet gas manifold at the top. The fiber bundle is rotated at high speed to provide pumping action, while oxygen flowing through the fiber bundle oxygenates the blood.

U.S. Pat. No. 5,830,370 to Maloney et al. describes a device having a fiber bundle mounted for rotation between a fixed central diffuser element and an outer wall of a housing. The fiber bundle is rotated at speeds sufficiently high to cause shear forces that induce turbulent flow within the blood. The patent does not address or even recognize the problem of blood trauma, i.e., hemolysis and platelet activation, that is expected to result from turbulent, high shear flow.

Although the devices described in the foregoing references offer some desirable features, those devices have numerous drawbacks that make them commercially impractical. These problems include: (a) introduction of small bubbles ("microbubbles") into the blood from the fiber due to higher gas side pressure relative to blood side pressure; (b) cavitation-induced blood trauma and damage to the device; (c) high shear loading leading to (i) buckling of the fibers or (ii) blood trauma; and (d) flooding of the inlet gas manifold, after fiber rupture, resulting in rapid reduction in oxygenation efficiency.

In view of the foregoing, it would be desirable to provide an extracorporeal blood pump/oxygenator that provides compact size, low priming volume, low surface area, and the ability to adequately oxygenate blood using a rotating fiber bundle that reduces boundary layer transfer resistance.

It would be desirable to provide an integrated extracorporeal blood pump/oxygenator having a hollow fiber bundle that oxygenates the blood and provides pumping action when rotated, but does not suffer from the leakage of gas into the blood, which leads to undesirable bubble formation.

It also would be desirable to provide an integrated extracorporeal blood pump/oxygenator having a hollow fiber bundle that oxygenates the blood and provides pumping action when rotated, but which overcomes microbubble generation problems observed in previously known integrated pump/oxygenator systems.

It further would be desirable to provide an integrated extracorporeal blood pump/oxygenator having a hollow fiber bundle design that does not generate high shear stresses, and thus is less susceptible to shear stress-induced fiber breakage and consequent leakage.

It would be further desirable to provide an integrated extracorporeal blood pump/oxygenator having a hollow fiber bundle design that reduces shear-induced blood trauma, including hemolysis and platelet activation.

It still further would be desirable to provide an integrated extracorporeal blood pump/oxygenator having a rotating hollow fiber bundle that is less susceptible to flooding of the gas manifolds than previously known designs.

It further would be desirable to provide an integrated extracorporeal blood pump/oxygenator having a low priming volume, thus making the system suitable for emergency back-up operation.

SUMMARY OF THE INVENTION

In view of the foregoing, it is an object of the present invention to provide an integrated extracorporeal blood pump/oxygenator having a compact size, low priming volume and the ability to adequately oxygenate blood using a rotating fiber bundle that reduces boundary layer resistance to gas transfer and the formation of stagnation zones within the fiber bundle.

It is another object of the present invention to provide an integrated extracorporeal blood pump/oxygenator having a low priming volume and low internal surface area, thereby reducing blood contact with non-native surfaces, potential damage to blood components, and the risk of infection.

It is yet another object of this invention to provide an integrated extracorporeal blood pump/oxygenator having a hollow fiber bundle that oxygenates the blood and provides a pumping action when rotated, but reduces the leakage of gas into the blood to form bubbles.

It is a further object of this invention to provide an integrated extracorporeal blood pump/oxygenator having a hollow fiber bundle that oxygenates the blood and provides a pumping action when rotated, but which overcomes microbubble generation problems observed in previously known integrated pump/oxygenator systems.

It is a still further object of the present invention to provide an integrated extracorporeal blood pump/oxygenator having a hollow fiber bundle that is less susceptible to breaking or buckling of the fibers due to high shear forces on individual elements of the fiber bundle and consequent leakage.

It is yet another object of the present invention to provide an integrated extracorporeal blood pump/oxygenator having a hollow fiber bundle design that reduces shear-induced blood trauma.

It is yet another object of this invention to provide an integrated extracorporeal blood pump/oxygenator having a rotating hollow fiber bundle that is less susceptible to flooding of the gas manifolds than previously known designs.

It is another object of the invention to provide an integrated extracorporeal blood pump/oxygenator having a low priming volume, thereby making the system suitable for emergency back-up operation.

These and other objects of the invention are accomplished by providing an integrated blood pump/oxygenator, suitable for use within a sterile field, that has a low priming volume. In accordance with the principles of the present invention, the pump/oxygenator includes a rotating hollow fiber bundle assembly that both oxygenates the blood and develops additional pressure head, if desired, to pump the blood. The device further includes one or more of the following improvements: means for reducing microbubble generation and blood trauma; means for reducing outward bowing of the fiber bundle; and means for reducing flooding of gas manifolds.

In a preferred embodiment, the integrated blood pump/oxygenator includes an tapered inner member disposed along a central shaft that increases pressure on the blood side relative to the gas side near the center of the fiber bundle, and, hence, prevents the formation of gas microbubbles in the blood. The inner member, which may optionally include helical vanes, also gradually accelerates blood prior to entering the fiber bundle, thereby reducing blood trauma. Shearing loads imposed on the fiber elements of the fiber bundle during high speed rotation are addressed by the addition of a reinforcement structure that extends around or within the fiber bundle. These reinforcement structures also assist in reducing shear stress imparted to the blood, hence reduce blood trauma. In addition, the gas manifolds of the pump/oxygenator optionally may be configured to reduce flooding and loss of efficiency due to occasional rupture of fiber elements.

Alternative embodiments of the integrated blood pump/oxygenator of the present invention may include a plurality of vanes for accelerating blood entering and/or exiting the fiber bundle. These vanes may be coupled to the same shaft that drives the rotating fiber bundle, or may optionally be driven at a different angular velocity using a separate drive train.

BRIEF DESCRIPTION OF THE DRAWINGS

Further features of the invention, its nature and various advantages will be more apparent from the accompanying drawings and the following detailed description of the preferred embodiments, in which:

FIGS. 8A and 8B are, respectively, perspective exterior and partial sectional views depicting a pump/oxygenator implementing the pre-accelerating vanes of FIG. 7 as a separate pre-pump element;

FIG. 9 is a side sectional view of the pre-pump element of the pump/oxygenator of FIGS. 8;

FIGS. 11A, 11B and 11C are, respectively, detailed views of the portions enclosed with boxes 11A and 11B of FIG. 10, and a perspective view of the of partitioned gas tube of FIG. 11A.

DETAILED DESCRIPTION OF THE INVENTION

The present invention provides an integrated blood pump/oxygenator that overcomes the drawbacks of previously known devices. In accordance with the principles of the present invention, the integrated system may be placed in or near the sterile field and has a low priming volume, e.g., 250 cc or less. A pump/oxygenator constructed in accordance with the principles of the present invention is expected to: (a) have little or no gas leakage into the blood and consequent bubble formation; (b) experience little or no cavitation, even at high speeds; (c) be less prone to rupture of fiber elements; (d) induce little or no blood trauma; and (c) provide adequate oxygenation capability even when occasional rupture of fiber elements occurs.

Figure 1:
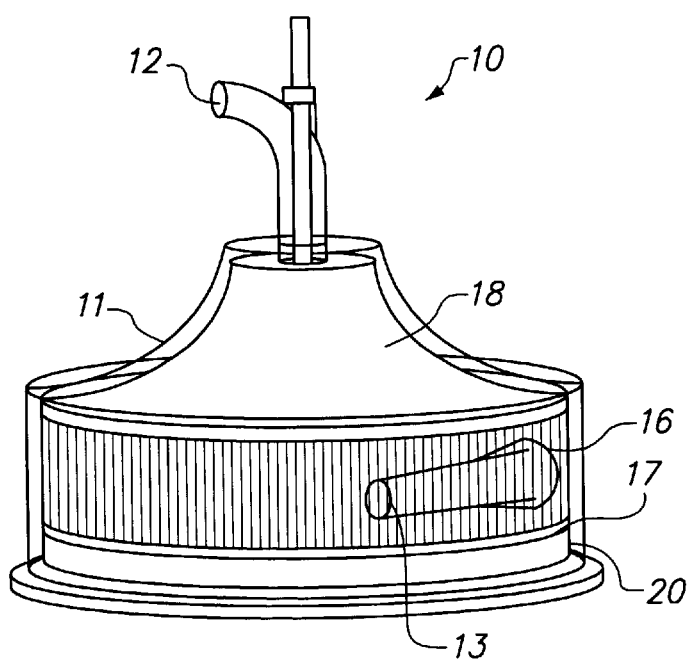
FIG. 1 is a perspective view of a previously known integrated blood oxygenator and pump system.
Figure 2:
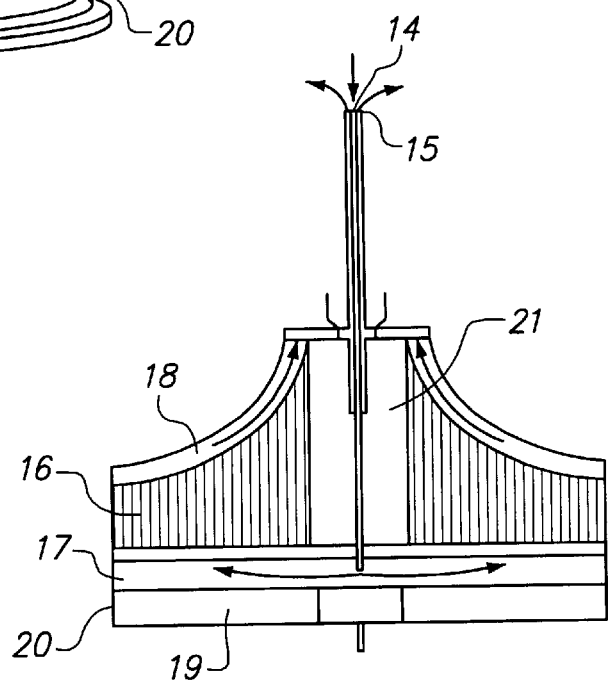
FIG. 2 is a side-sectional view of the pump/oxygenhator of FIG. 1.

Referring to FIGS. 1 and 2, previously known integrated blood oxygenator/pump 10 of the above-mentioned Makarewicz et al. article entitled, "New Design for a Pumping Artificial Lung," which is incorporated herein by reference in its entirety, is described. Pump/oxygenator 10 comprises sealed housing 11 having blood inlet 12, blood outlet 13, gas inlet 14 and gas outlet 15. Hollow fiber bundle 16 is potted to inlet gas manifold 17 at the bottom and outlet gas manifold 18 at the top. The hollow fiber bundle is substituted for the vanes of a BIOMEDICUS® blood pump (a registered trademark of Bio-Medicus, Eden Prairie, Minn.). As will be familiar to one of ordinary skill in the art of cardiopulmonary bypass, the Bio-Medicus pump includes a magnet 19 disposed in tray 20 which is magnetically coupled to a magnet affixed to a drive shaft (not shown).

Blood entering pump/oxygenator 10 through inlet 12 passes into central void 21. When fiber bundle 16 is rotated, blood is drawn by centrifugal force into fiber bundle 16, accelerates as it passes through the fiber bundle, and exits the pump/oxygenator through blood outlet 13. Oxygen flows through gas inlet 14 to manifold 17, from which it is distributed to the individual fibers of the fiber bundle. As the blood passes through fiber bundle 16, carbon-dioxide diffuses into the fibers through the microporous walls of the hollow fibers, while oxygen diffuses from the fiber bundle into the blood. The remaining oxygen and carbon-dioxide pass into outlet gas manifold 18, and from there may be vented to the atmosphere through gas outlet 15.

While the pump/oxygenator of FIGS. 1 and 2 provides some highly desirable features, including a low priming volume and small surface area, applicants have determined that the device has a number of drawbacks that render it commercially infeasible. Applicants also have discovered, however, various improvements that overcome those drawbacks, and expect that the improvements described hereinafter will enable pump/oxygenators similar to that of FIGS. 1 and 2 to become commercially feasible products.

A first drawback of the device of FIGS. 1 and 2 is the tendency of rotation of the fiber bundle to generate microbubbles, i.e., induce low pressure regions that draw gas bubbles through the microporous membrane from the gas-side to the blood-side. Specifically, rotation of fiber bundle 16 causes a low pressure region to form in central core 21, which in turn pulls gas bubbles through the membrane of the fiber elements nearest the center. In addition, formation of localized low pressure regions may induce classical cavitation, i.e., generation of a vapor phase in the form of microbubbles. The bubbles not only pose an inherent risk, if not filtered out prior to perfusion of the patient, but also may cause the blood to froth, thereby decreasing oxygenation efficiency.

A second drawback of the device of FIGS. 1 and 2 is that during rotation of the fiber bundle, the individual fiber elements tend to bow radially outward. Depending upon the rotational speed of the fiber bundle, the forces developed in the fiber bundle may become so high that the fibers frequently either tear free from the potting or rupture. This in turn causes leakage of blood into the inlet gas manifold.

Leakage from loose or ruptured fibers may cause a third and significant problem in the above-described previously known device. Specifically, large amounts of blood leaking into inlet gas manifold 17 or outlet gas manifold 18 through the ruptured or loose fibers may cause these gas manifolds to flood, thereby cutting off the oxygen supply to the fiber bundle and rendering the device inoperative.

Moreover, even if blood leaks into the gas manifolds through relatively few of the fibers, rotation of the fiber bundle causes the blood to be urged radially outward and pool along the outer circumference of the fiber bundle 16. This pooled blood in turn cuts off the fiber elements from gas flow. Because the area adversely affected by the pooled blood is directly proportional to the radius, flooding at the outer edge of the fiber bundle leads to a rapid decrease in oxygenation efficiency.

Yet another serious drawback of the device of FIGS. 1 and 2 is that the high shear imparted to the blood results in undesirable blood trauma, including hemolysis and platelet activation. This high shear stress and resulting blood trauma are encountered primarily where the blood enters and exits the fiber bundle. Upon entering the fiber bundle, the blood collides with the rapidly rotating fibers of the fiber bundle, and is therefore rapidly accelerated by these collisions. Also, as the blood exits the fiber bundle, it is exposed to high shear levels at the boundary between the fiber bundle and the inner wall of the housing. This especially may be so in the presence of outward bowing of the fiber bundle, where the bowing results in reduced clearance between the exterior of the fiber bundle and the inner wall of the housing.

Figure 3:
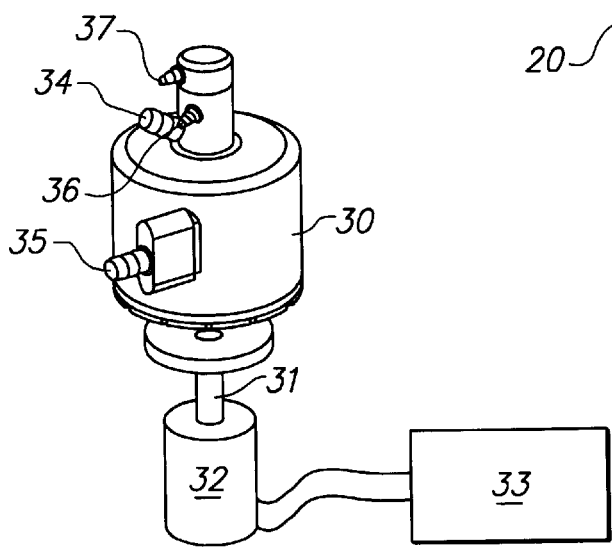
FIG. 3 is a schematic view of an integrated constructed in accordance with the preseat invention.
Figure 4A:
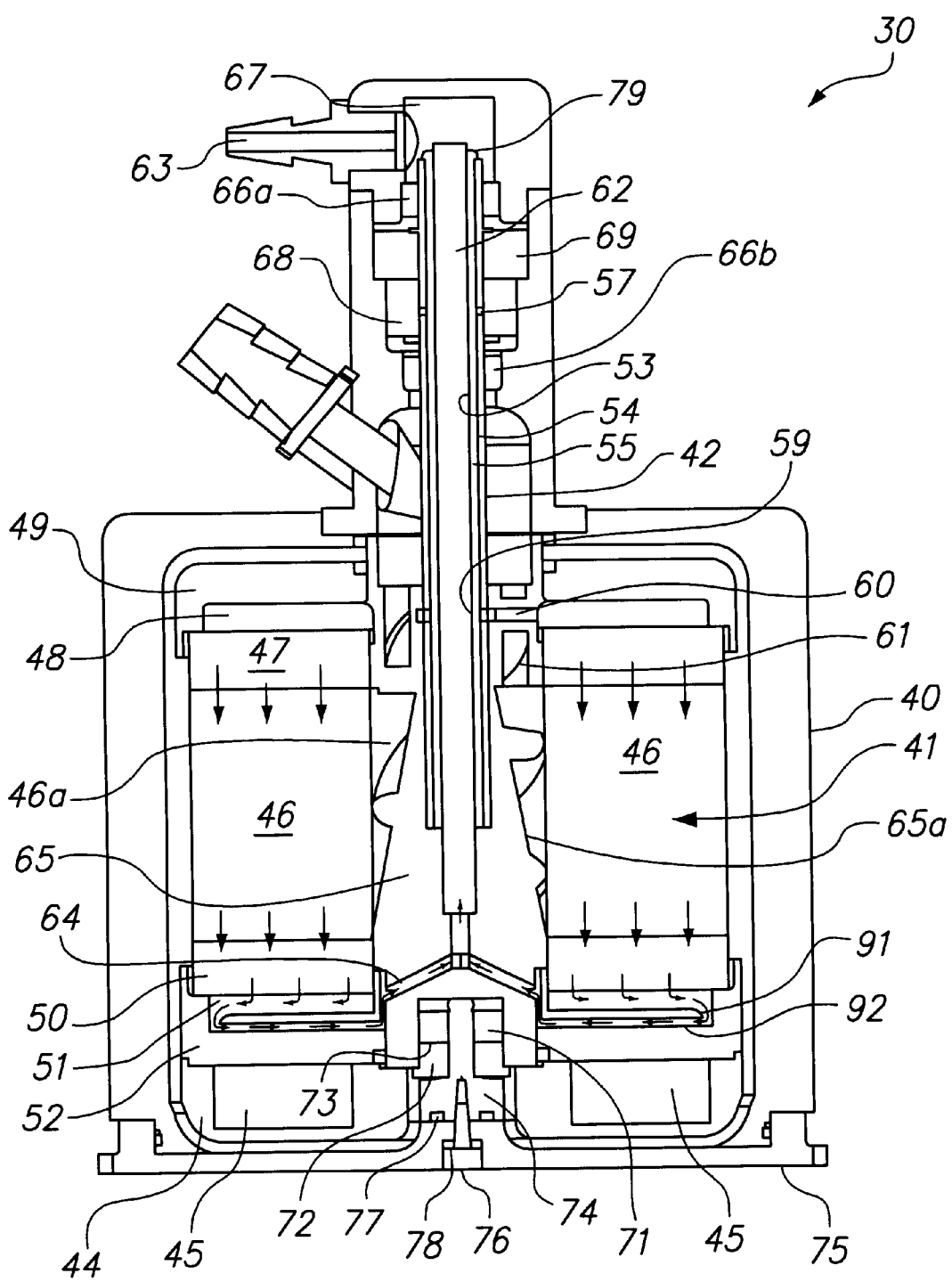
FIG. 4A and 4B are, respectively, side-sectional and cut-away views of the pump/oxygenator of FIG. 3.
Figure 4B:
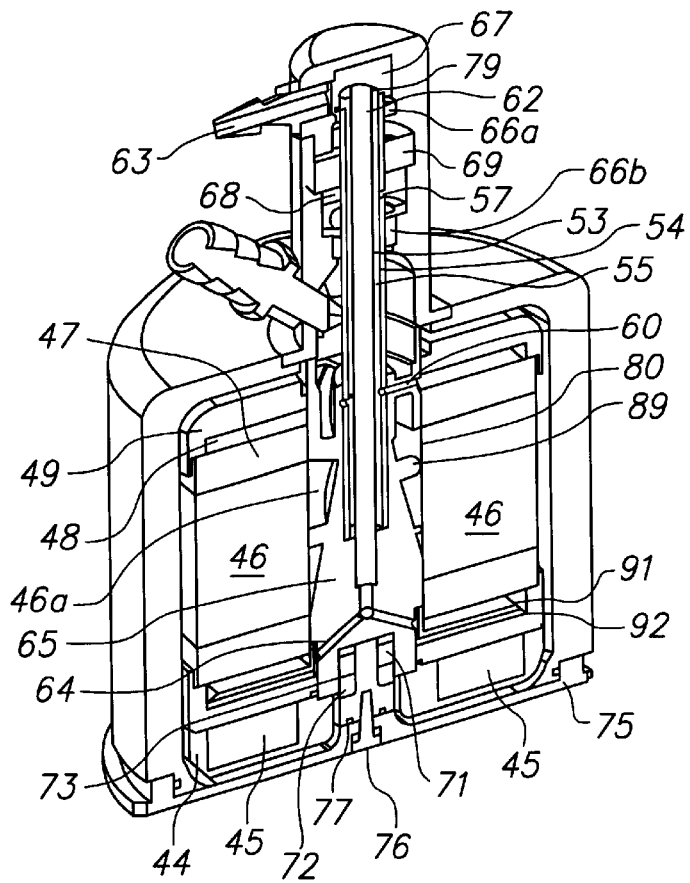

Referring now to FIG. 3, apparatus constructed in accordance with the present invention is described. Pump/oxygenator 30 of the present invention includes several improvements over the device described in the above-incorporated Makarewicz et al. paper, useful individually or in combination, that overcome the problems described hereinabove. Pump/oxygenator 30 is magnetically coupled to drive shaft 31 of motor 32, which is in turn controlled by controller 33. Deoxygenated venous blood is supplied to pump/oxygenator 30 via suitable biocompatible tubing (not shown) coupled to venous blood inlet 34; oxygenated blood is returned to the patient from pump/oxygenator 30 via biocompatible tubing (not shown) coupled to blood outlet 35.

Pressurized oxygen is introduced into pump/oxygenator 30 via gas inlet port 36, while a mixture of oxygen and carbon dioxide exits pump/oxygenator 30 via gas outlet port 37. Motor 32, magnetically coupled drive shaft 31 and controller 33 are items per se known in the art, and may comprise any of a number of systems available from Bio-Medicus, Inc., Eden Prairie, Minn. Alternatively, drive shaft 31, motor 32 and controller 33 may be miniaturized to permit their placement closer to the patient.

Referring now to FIGS. 4A–4B and 5A–5D, the internal arrangement of integrated pump/oxygenator 30 of the present invention is described. Pump/oxygenator 30 comprises housing 40 enclosing a gas transfer element in the form of fiber bundle assembly 41 that rotates within housing 40 on shaft 42. Shaft 42 is affixed to shaft impeller 65, which is attached to tray 44. Tray 44 holds one or more magnets 45 that are used to magnetically couple fiber bundle assembly 41 to drive shaft 31 (see FIG. 3).

Fiber bundle 46 preferably comprises an annular shape formed from a multiplicity of microporous hollow fiber elements, and includes a central void 46a. The upper ends of the hollow fiber elements are potted in region 47, so that the interior lumens of the fibers communicate with void 48 in inlet gas manifold 49. Likewise, the lower ends of the hollow fiber elements of fiber bundle 46 are potted in region 50, so that the interior lumens of the fibers communicate with void 51 in outlet gas manifold 52. Any of a number of suitable biocompatible potting materials may be used, such as polyurethanes or epoxies.

Shaft 42 includes inner tube 53 and outer tube 54 arranged coaxially to form annulus 55. Annulus 55 communicates with gas inlet port 36 (shown in FIG. 3) via through-wall holes 57, and with void 48 of inlet gas manifold 49 via through-wall holes 59 and passageways 60 in plurality of pumping vanes 61. Lumen 62 of inner tube 53 communicates with gas outlet port 63 at its upper end and void 51 in outlet gas manifold 52 at its lower end via passageways 64 in shaft impeller 65. Shaft seal 66a separates space 67, which couples gas outlet port 63 to lumen 62, from space 68, which couples gas inlet port 36 (shown in FIG. 3) to annulus 55. Shaft seal 66b separates space 68 from the interior of housing 40, which encloses fiber bundle assembly 41. Shaft seals 66a and 66b are retained with seal caps 66c and 66d, respectively (see FIG. 5A).

Shaft 42 is carried in bearing 69, while shaft impeller 65 is carried on bearings 71 and 72. Thrust washer 73 is interposed between bearings 71 and 72, and the entire assembly is in turn carried on bearing shaft 74. Bearing shaft 74 is affixed to lower plate 75 of housing 40 by shoulder screw 76, and is seated on O-ring seal 77. Shoulder screw 76 also is sealed with O-ring 78. Shaft impeller 65 seals the lower end of annulus 55, while the upper end of the annulus is sealed by plug 79.

Figure 5A:
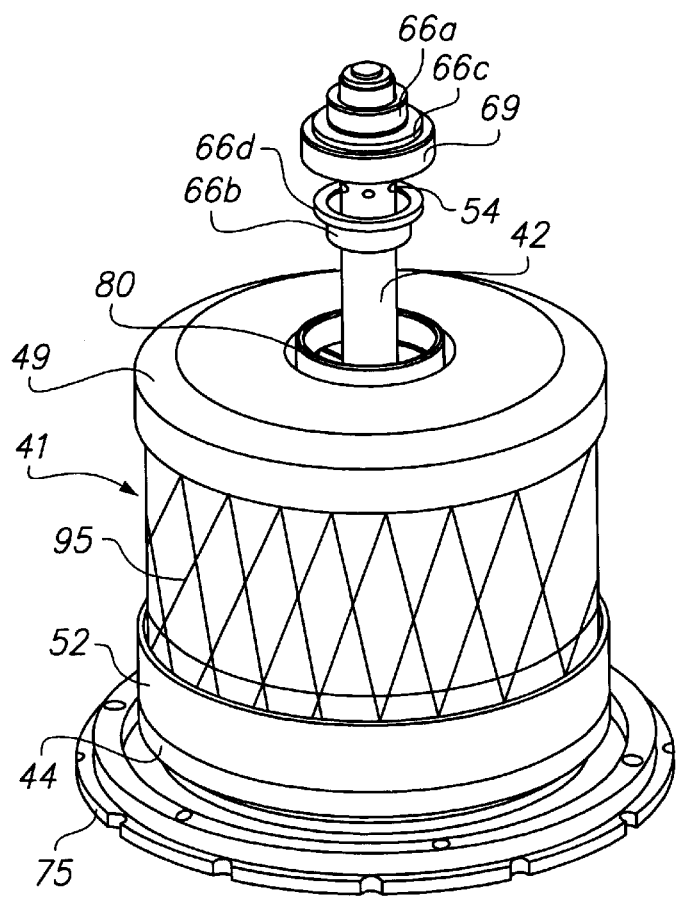
FIGS. 5A–5D are perspective views of the internal components of the pump/oxygenator of FIG. 3.
Figure 5B:
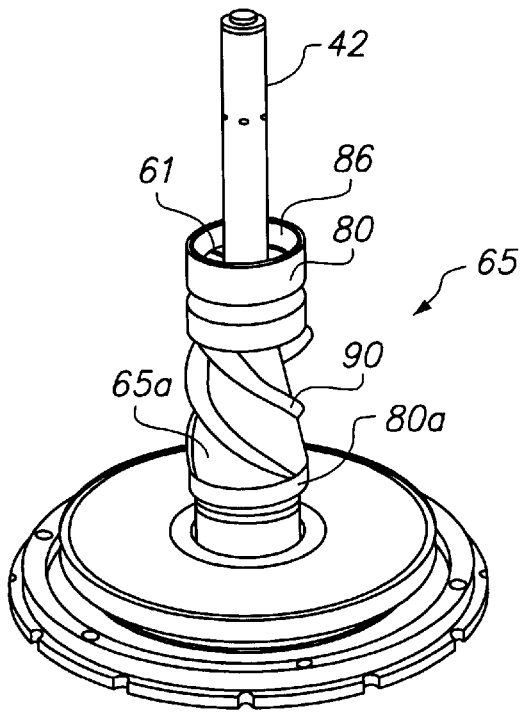
Figure 5C:
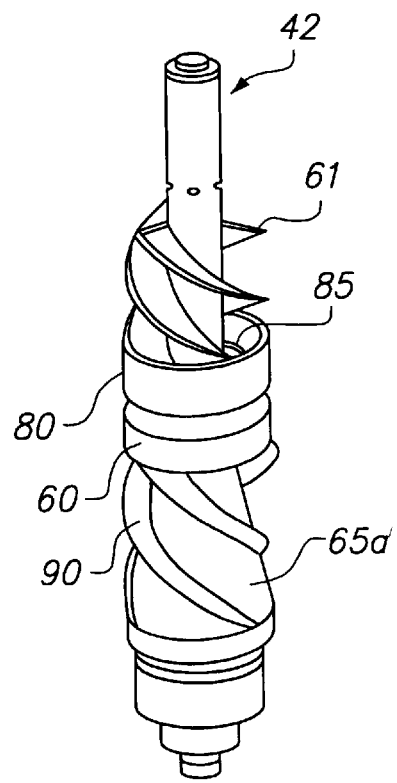

Shaft impeller 65 (shown in FIG. 5B) forms an inner member that radially displaces blood entering the central void 46a, and comprises upper hub 80 and lower hub 80a. Upper hub 80 is connected to upper potting 47 and lower hub 80a is connected to lower potting 50. Pumping vanes 61 optionally may be incorporated on hub 80, and extend helically downwards to form vanes 90. FIG. 5C shows an alternate embodiment of shaft impeller 65, where pumping vanes 61 optionally also extend above hub 80. Openings 85 between the plurality of vanes 61 permit blood entering pump/oxygenator 30 via venous blood inlet 86 to flow into fiber bundle 46. Vanes 61 are configured to serve as vanes that pump and accelerate blood passing through the fiber bundle 46. As will of course be appreciated, the pump housing and seal locations must be appropriately modified to accommodate extended vanes 61 of FIG. 5C.

In accordance with the principles of the present invention, pump/oxygenator 30 includes a number of features that overcome drawbacks observed in the device of FIGS. 1 and 2. These improvements may be used individually, or in combination, depending upon the intended application of the pump/oxygenator.

To reduce microbubble generation and shear-induced blood trauma of the previously known devices shown in FIGS. 1 and 2, conically tapered portion 65a of shaft impeller 65 is provided to increase the blood side pressure between hubs 80 and 80a. Optionally, pluralities of vanes 61 and 90 may be disposed on impeller shaft 65 to further reduce the bubbling observed in previously known devices at higher speeds by increasing the pressure of blood entering fiber bundle 41. Tapered portion 65a of shaft impeller 65 also is expected to reduce blood trauma by imparting a gradual acceleration to blood entering the hollow fiber bundle, and thus reduce high shear forces encountered in previously known designs when the blood impinges upon the rotating bundle. In addition, or alternatively, the pressure at which the blood is supplied to pump/oxygenator 30 may be increased, for example, using an auxiliary pre-pump, as described hereinafter with respect to FIG. 7–11.

To reduce the flooding problems encountered in the previously known device of FIGS. 1 and 2, the positions of the inlet and outlet gas manifolds optionally may be reversed (relative to the design of FIGS. 1 and 2), so that void 51 formed by outlet gas manifold 52 is coupled to lumen 62 of inner tube 53. In addition, baffle plate 91 may be disposed in void 51, and includes grooves 92 on its underside that communicate with passageways 64. Baffle plate 91, if present, causes gas exiting fiber bundle 46 to pass around the outermost edge of the baffle plate. Accordingly, blood leaking into void 51 of the outlet gas manifold is cleared from the manifold and entrained in the exhaust gas stream passing through gas outlet port 63.

To reduce stress-induced failure of fibers, and to reduce the fibers pulling free of the potting material, as encountered in previously known devices, a support structure preferably is disposed around the fiber bundle assembly 41. Referring to FIG. 5A, fiber bundle assembly 41 and shaft 42 are shown without housing 40. Girdle 95, which may comprise a collar or sleeve made of a suitable biocompatible material, such as a metal or plastic, is disposed around the circumference of fiber bundle 46. Girdle 95 preferably is potted with the fiber bundle in the inlet and outlet gas manifolds.

In accordance with the principles of the present invention, girdle 95 reduces radially outward bowing of the fiber elements of fiber bundle 46 when pump/oxygenator 30 is operated at high speed. Girdle 95 therefore reduces the strain imposed on the fiber elements, prevents the fiber elements from contacting the interior surface of the housing, and reduces the risk that fiber elements will pull free from the potting material or otherwise rupture. Because girdle 95 is expected to reduce the number of fiber elements that rupture, it is therefore expected to reduce the risk of flooding. In combination with baffle plate 91 and the reversed gas flow path described above, it is expected that pump/oxygenator 30 will maintain high gas exchange efficiency even in the presence of a nominal number of ruptured fibers.

Figure 5D:
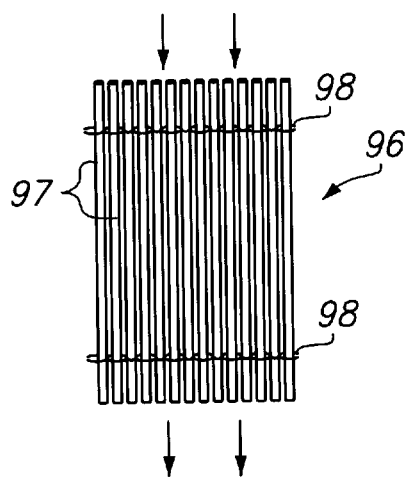

Referring to FIG. 5D, fiber bundle 46 (see FIG. 4A) preferably comprises hollow fiber mat 96 comprising a multiplicity of fibers 97 interconnected by threads 98. In one preferred embodiment, fiber bundle 46 is formed by wrapping hollow fiber mat 96 about hubs 80 and 80a, and then sealing the free end of the mat against the next-inner layer using a suitable biocompatible adhesive. Girdle 95 may then be disposed about the circumference of the fiber bundle, as described hereinabove with respect to FIG. 5A. Alternatively, or in addition to girdle 95, the fiber bundle may be reinforced by gluing or heat-sealing overlapping regions of the fiber mat together. By aligning such glued regions radially, it is expected that the structural integrity of the fiber bundle will be increased sufficiently to reduce outward bowing, but without adversely impacting outward movement of blood through the fiber bundle.

In addition, the foregoing support structures assist in reducing blood trauma by maintaining a proper spacing between the exterior surface of the fiber bundle and the inner wall of the housing. Specifically, these structures apply a radially inwardly directed force that and are expected to avoid high shear stresses that may be imposed on the blood where a bowed out section of the fiber bundle rotates too closely to, and/or contacting, the inner wall of the housing.

Figure 6:
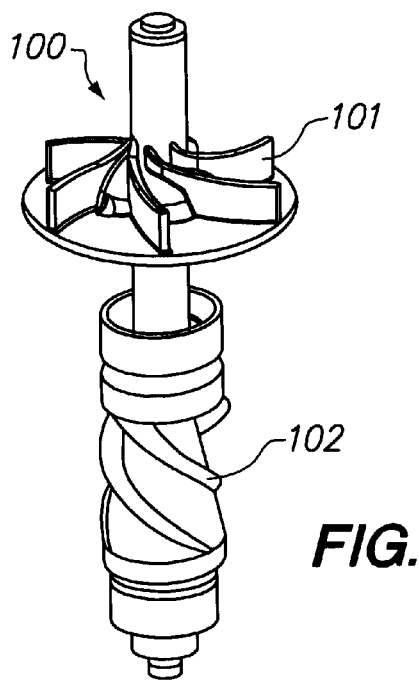
FIG. 6 is a partial perspective view of an alternative-embodiment of a shaft suitable for use in the pump/oxygenator of the present invention.

Referring now to FIG. 6, shaft 100 suitable for use in an alternative embodiment of the present invention is described. Shaft 100 is similar in construction to shaft 42 of FIG. 5C, except that shaft 100 includes a plurality of vanes 101 disposed above pumping and accelerating vane 102. Vanes 101 are designed to increase the pressure of blood flowing along shaft 100 thereby further reducing the potential for cavitation, bubbling and blood trauma during high speed operation. As will of course be appreciated, the pump housing must be modified to accommodate vanes 101, and the number, shape and orientation of vanes 101 may be empirically selected to provide an adequate flow rate and pressure head and to further reduce blood trauma.

Figure 7:
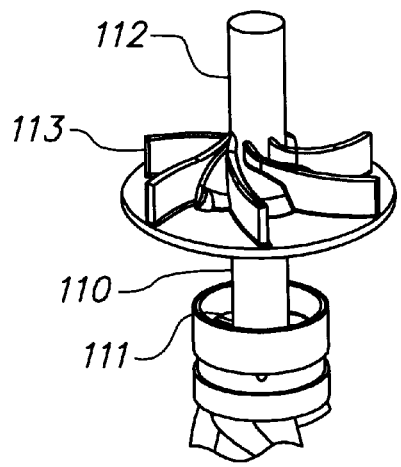
FIG. 7 is a partial perspective view of a further alternative embodiment of a shaft and impeller arrangement suitable for use with the present invention.

In FIG. 7, a further alternative embodiment of a pre-accelerating vane is illustrated. In this embodiment, shaft 110 and accelerating vanes 111 serve the functions described hereinabove with respect to tapered portion 65a of shaft impeller 65 of the embodiment of FIGS. 4 and 5. Shaft 112 comprises a hollow tube that is arranged coaxially with shaft 110, and includes a plurality of vanes 113. Shaft 112 may be driven at the same or a different angular velocity than shaft 110, for example, by suitable gearing or a separate motor via a belt arrangement, so that the amount of pre-acceleration provided by vanes 113 may be varied as a function of the rotational speed of the fiber bundle. The number, orientation and shape of vanes 113 may be determined empirically, while other modifications to pump/oxygenator 30 needed to implement this variation will be apparent, to one of ordinary skill in the art of pump design, from inspection.

Alternatively, or in addition, vanes 113 and housing 40 may be configured so that vanes 113 and shaft 112 function as a separate pump, the outlet of which may be directed into the fiber bundle via accelerating vane 111, or directed back to perfuse the patient, via suitable valving. In this manner, the pump/oxygenator of the present invention may be used to partially unload a heart, for example, during beating heart surgery, followed by placing the patient on full cardiopulmonary bypass for a phase of the surgery where the heart is stopped.

Referring now to FIGS. 8–11, a preferred embodiment implementing the plurality of vanes 113 of FIG. 7 as a separate pre-pump element is described. With respect to FIGS. 8A and 8B, pump/oxygenator 120 constructed in accordance with the principles of the present invention is described wherein microbubble generation within the central void of the gas transfer element is reduced using a separately driven pre-pump. Pump/oxygenator 120 also illustratively includes a heat exchanger for heating or cooling blood, depending upon the phase of the cardiac surgery. Pump/oxygenator 120 preferably is magnetically coupled to motor drives 121a and 121b, which are programmably controlled by controller 122. Controller 122 includes microprocessor 123 and display/input console 124, and may comprise, for example, an LCD screen and keyboard.

Referring to FIG. 8A, pump/oxygenator 120 includes housing 125 having compartment 126 that houses rotating fiber bundle 127 and compartment 128 that houses centrifugal pump 129. Compartment 128 preferably is coupled to compartment 126 by passageway 130, so that the outlet of centrifugal pump 129 is directed into central void 131 of fiber bundle 127. Blood enters device 120 via blood inlet 132 and exits via blood outlet 133.

An oxygen-rich gas mixture enters via gas inlet port 134 and the oxygen-depleted, carbon dioxide-rich exhaust gas exits via gas outlet port 135. Heated or cooled water (depending upon whether it is desired to warm or cool the blood as required for a given phase of a surgery) enters coiled tube 136 via water inlet port 137 and exits via water outlet port 138. Port 139 may be used to vent air from compartment 126 during priming of device 120, and optionally may be used to introduce fresh blood in compartment 126 to wash out stagnant blood, e.g., if the fiber bundle is permitted to remain stationary during a cardiac procedure. Blood pressure within the central void of fiber bundle 127 may be monitored, and gas accumulating within central void 131 may be vented, via vent port 140. Applicants have observed that during prolonged operation of a rotating fiber bundle device, such as depicted in FIGS. 4 and 8, such microbubbles as are formed in the device tend to coalesce near the center of central void 131. Vent port 140 and line 141 coupled thereto extend within the upper portion of central void 131 and advantageously may be used to vent whatever gas collects within pump/oxygenator 120.

With respect to FIG. 9, centrifugal pump 129 comprises impeller 145 having a plurality of vanes 146 mounted on hub 147 adjacent to central flow diverter 148. Impeller 145 is mounted on magnet tray 149 that holds permanent magnet 150. Blood entering via blood inlet port 132 experiences a rise in pressure and radial velocity caused by rotation of impeller 145, and exits compartment 128 via passageway 130, where the blood is directed into central void 131 of fiber bundle 127. Centrifugal pump 129 is magnetically coupled to a corresponding permanent magnet or electromagnet in motor drive 121a, so that impeller 145 can be rotated at a desired angular velocity to provide a selected pumping head and flow rate.

With respect to FIGS. 8A, 10 and 11A–11C, fiber bundle 127 is mounted within compartment 126 for rotation at a desired angular velocity when driven by motor drive 121b, as described hereinbelow. In particular, fiber bundle 127 comprises a multiplicity of hollow fiber elements disposed surrounding central void 131. The lower ends of the fiber elements are coupled by potting ring 155 to inlet gas manifold 156, and communicate with void 157, while the upper ends of the fiber elements are coupled by potting ring 158 to gas outlet manifold 159 and communicate with void 160. Fiber bundle 127 is mounted for rotation in compartment 126 at the lower end on shaft 161 and at the upper end on partitioned tube 162. Shaft 161 is coupled to shaft 163, which in turn rotates in bearing 164, while partitioned tube rotates in bearing 165.

With respect to FIG. 11C, partitioned tube 162 preferably comprises a stainless steel shaft having central bore 166, gas inlet lumens 167 and gas outlet lumens 168. Lumens 167 and 168 are closed at either end, and communicate with the exterior of the shaft via semi-circular notches 169a and 169b, and 170a and 170b, respectively. Partitioned tube 162 is disposed in housing 125 so that notch 169a communicates with chamber 171, into which oxygen-rich gas is introduced via gas inlet port 134. The oxygen-rich gas passes downward through gas inlet lumens 167 and exits tube 162 via notch 169b. Notch 169b communicates with cavity 172 which is described in greater detail hereinbelow. Gas exhausted through the upper end of fiber bundle 127 into void 160 enters tube 162 via notch 170a, passes through gas outlet lumens 168, and exits tube 162 via notch 170b. Notch 170b communicates with cavity 173, which in turn communicates with gas outlet port 135. Blood exiting centrifugal pump 129 via passageway 130 enters the central void 131 of fiber bundle 127 through bore 166 of partitioned tube 162.

Figure 10:
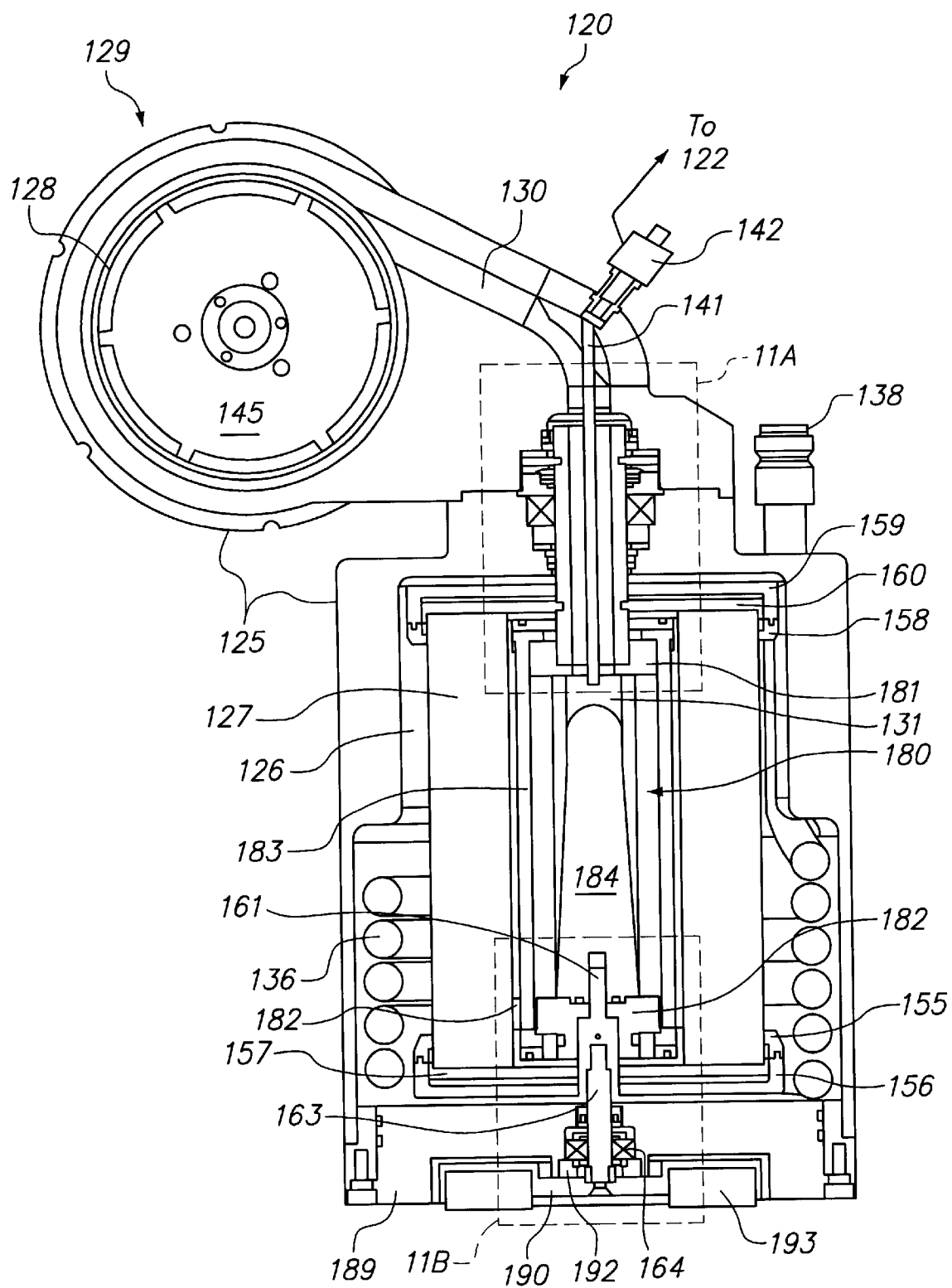
FIG. 10 is a side sectional view of the pump/oxygenator component of the device of FIGS. 8.

Referring now to FIGS. 10 and 11, fiber bundle 127 includes support structure 180 disposed within central void 131. Support structure 180 comprises upper hub 181, lower hub 182, connecting rods 183 and tapered inner member 184. Upper hub 181 includes an annular groove forming cavity 172, a plurality of radially directed passages 185 and a plurality of vertical bores 186 that intersect the radially directed passages 185 (see FIG. 11A). Lower hub 182 likewise includes a plurality of vertically directed bores 187 that communicate with an annular groove portion of void 157 via radially directed bores 188 (see FIG. 11B). Connecting rods 183, which are hollow, are mounted with their upper ends in respective ones of the vertical bores 186 of upper hub 181 and their lower ends in respective ones of vertical bores 187 of lower hub 182. In this manner, gas introduced into cavity 172 through notch 169b passes through bores 185 and 186 of upper hub 181, through connecting rods 183, through bores 187 and 188 of lower hub 182, and into void 157 formed by potting ring 155 and gas inlet manifold 156.

Accordingly, oxygen-rich gas introduced through gas inlet port 134 is conducted to void 157, from which the gas travels through the multiplicity of hollow fiber elements comprising fiber bundle 127. Gas exiting through the upper ends of the fiber elements into void 160 enters gas outlet lumens 168 via notch 170a in partitioned tube 162, and then passes through notch 170b and cavity 173 to gas outlet port 135.

In accordance with the principles of the present invention, tapered inner member is disposed within support structure 180 and central void 131, and is coupled to lower hub 182. Blood entering central void 131 through bore 166 of partitioned tube 162 impinges upon inner member 184, and is gradually displaced radially outward by the tapered surface of the inner member. Like tapered portion 65a of impeller shaft 65 of the embodiment of FIG. 4, inner member 184 reduces the priming volume of the device, and reduces blood trauma both by increasing pressure within the central void (and thus reducing microbubble generation) and by gradually accelerating blood entering the void to the angular velocity of the surrounding fiber bundle.

Applicant has observed that during operation of prototype devices having a rotating fiber bundle, such as depicted in FIG. 4, what microbubbles do form tend to coalesce along the axis of the central void. Vent tube 141 therefore is provided having a lower end that communicates with the upper portion of the central void 131, so that any gas bubbles coalescing in the central void may be vented, thereby further reducing the risk that gas bubbles will be carried downstream. In addition, vent tube 141 and vent port 140 may be used to measure blood pressure within the central void of the fiber bundle. The blood pressure also may be measured with pressure transducer 142 mounted to vent tube 141 (see FIG. 10). This information, together with the fiber bundle rotational velocity, inlet gas pressure and head supplied by pre-pump 129 may then be used to control microbubble formation in compartment 126.

As in the preceding embodiments, lower hub 182 is coupled to magnet tray 190 by shafts 161 and 163, and drive pins 191. Magnet tray 190 preferably holds permanent magnet 193 that magnetically couples the fiber bundle to motor drive 121b, so that rotational motion can be transferred to fiber bundle 127. As describe hereinbelow, centrifugal pump 129 and fiber bundle 127 preferably are driven at different angular velocities that are selected or coordinated by controller 122 to optimize some feature of the pump/oxygenator, such as minimizing microbubble generation.

In accordance with a preferred aspect of the present invention, the rotational speeds of centrifugal pump 129 and fiber bundle 127 are selected or coordinated so that, over a range of blood flow rates and for a range of gas inlet pressures, the oxygenation level of blood passing through pump/oxygenator 120 can be optimized, while limiting microbubble formation and associated blood trauma. Thus for example, microprocessor 123 of controller 122 may be programmed with suitable empirically derived algorithms that relate gas inlet pressure, and rotational speeds of the pre-pump and fiber bundle, to obtain at least a local maximum in blood oxygenation for a given flow rate, as follows:

$$H_{pre-pump} = f_1(\omega_1) \tag{1}$$

$$F_E = f_2(\omega_1, \omega_2) \tag{2}$$

$$O_2 = f_3(F_E, \omega_1, \omega_2, \rho_I, \rho_o) \tag{3}$$

$$B_{gen} = f_4(H_{pre-pump}, O_2, T_I, T_o) \tag{4}$$

wherein:

$H_{pre-pump}$ is the pressure head developed by pre-pump 129;

$f_1(\ )$ is an empirically derived function that describes the interrelationship between the centrifugal pump rotational speed $\omega_1$, and the pre-pump head for given dimensions of the pump/oxygenator 120;

$F_E$ is the flow rate at the blood outlet port 133;

$f_2(\ )$ is an empirically derived function that describes the interrelationship between the centrifugal pump rotational speed $\omega_1$, the fiber bundle rotational speed $\omega_2$, and blood flow rate;

$O_2$ is the oxygenation rate of blood exiting blood outlet port 133;

$f_3(\ )$ is an is an empirically derived function that describes the interrelationship between the flow rate at the blood outlet port $F_E$, the centrifugal pump rotational speed $\omega_1$, the fiber bundle rotational speed $\omega_2$, and the gas inlet and gas outlet pressures $\rho_I$, $\rho_o$, respectively;

$B_{gen}$ is the microbubble generation rate; and $f_4(\ )$ is an is an empirically derived function that describes the interrelationship between the microbubble generation rate, the pre-pump pressure head, the oxygenation level, and, optionally, the temperatures of fluid circulated through coil 136 at the water inlet port 137 and water outlet port 138.

Applicant expects that by running suitable parametric studies of the pump/oxygenator 120, i.e., where one or more variables are held constant and the remaining variables are varied over a range, functions $f_1(\ )$, $f_2(\ )$, $f_3(\ )$ and $f_4(\ )$ may be readily determined. The resulting curves may be generated using multi-variate equation processing techniques, well-known in the art, to interpolate or extrapolate the behavior of pump 120 for a given set of inputs. Local optima also may be determined, for example, to maximize oxygenation level with the minimum fiber bundle speed, so as to minimize blood trauma. It will be apparent that other analyses could be advantageously undertaken to optimize the performance of device 120.

Accordingly, controller 122 may be programmed with the algorithms determined as described hereinabove, so that, for a given desired blood flow rate and oxygenation level at blood outlet port 133, the rotational speeds of the pre-pump and fiber bundle are optimized to reduce blood trauma and microbubble generation. Alternatively, other optimization strategies may be advantageously employed, such as minimizing the centrifugal loads placed on the fiber elements of fiber bundle 127 by always rotating the fiber bundle at the lowest rotational speed permissible to achieve a desired blood flow rate and oxygenation level.

In a preferred embodiment, pressure sensor 142 (see FIG. 10) is coupled to controller 122 to provide a signal corresponding to the blood pressure within central void 131. The signal output by the sensor is used by controller 122 to select or coordinate the speeds of drive motors 121a and 121b so as to ensure that the blood pressure within the central void is maintained at a level greater than a level at which significant microbubble generation is detected.

Figure 12:
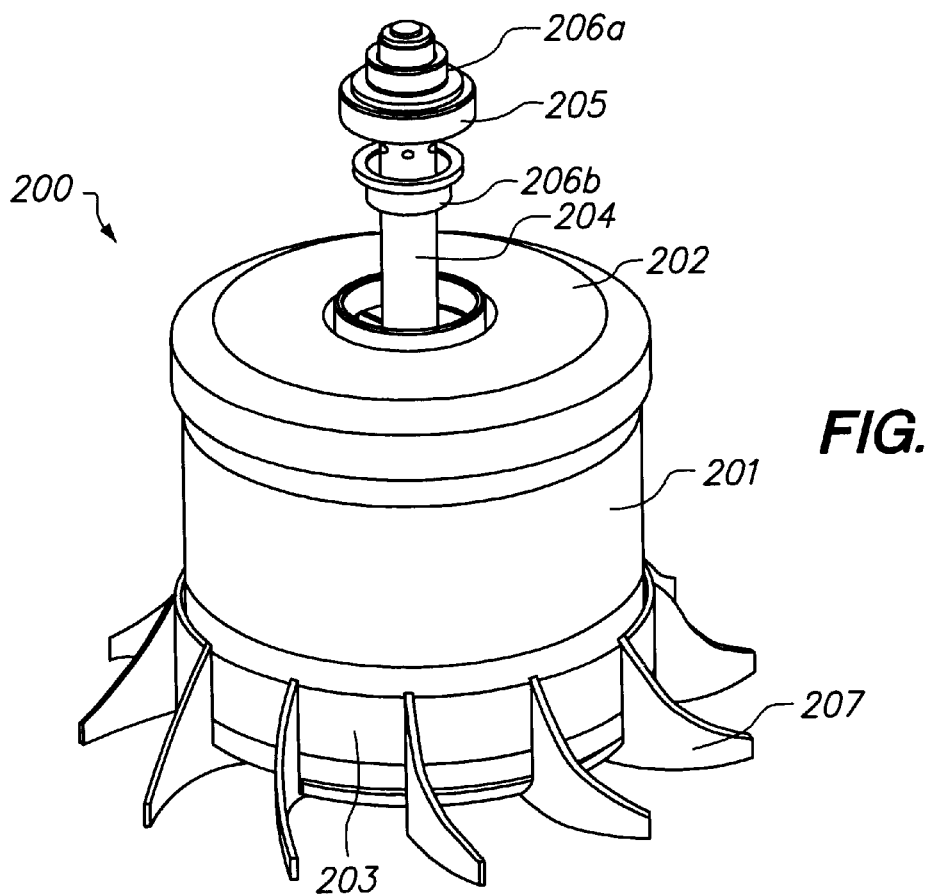
FIG. 12 is a partial view of a further alternative embodiment of an internal assembly suitable for use in a pump/oxygenator of the present invention.

Referring now to FIG. 12, internal assembly 200 of another alternative embodiment of the pump/oxygenator of the present invention is described. Assembly 200 includes fiber bundle 201 having inlet and outlet gas manifolds 202 and 203, and is mounted on shaft 204 with bearing 205 and shaft seals 206a and 206b, as described hereinabove with respect to the embodiment of FIGS. 4 and 5. Assembly 200, however, further includes vanes 207 mounted in fixed relation to, and that rotate with, the fiber bundle. Vanes 207 are provided to increase the pressure head developed by the pump/oxygenator. Specifically, blood exiting fiber bundle 201 impinges upon vanes 207 and is further accelerated as it exits the pump/oxygenator. As will of course be apparent, the housing must be modified to accommodate vanes 207, while the number, orientation and shape of vanes 207 may be selected to provide a desired degree of additional pressure head and to minimize blood trauma.

The integrated blood pump/oxygenators of the present invention illustratively have been described as employing magnetic couplings. The present invention, however, may be readily adapted for use with other drive systems. For example, the magnet tray may be replaced with a direct motor drive, or may be coupled by a cable to a drive system and control console located outside the sterile field. Such a direct drive system could be miniaturized to be accommodated within the sterile field. Furthermore, the controls could be operated remotely using infrared or other such remote controlling means. The integrated blood pump/oxygenator of the present invention could also be incorporated into a standard cardiopulmonary bypass system that has other standard components such as a heat exchanger, venous reservoir, arterial filter, surgical field suction, cardiac vent, etc.

While preferred illustrative embodiments of the invention are described above, it will be apparent to one skilled in the art that various changes and modifications may be made therein without departing from the invention and it is intended in the appended claims to cover all such changes and modifications which fall within the true spirit and scope of the invention.

What is claimed is:

1. A system for processing blood comprising:
a housing having a gas inlet, a gas outlet, a blood inlet and a blood outlet;
a fiber bundle disposed for rotation within the housing, the fiber bundle having a central void in fluid communication with the blood inlet; and
an inner member disposed within the central void, the inner member being rotatable relative to the housing, the inner member having a length and being tapered along the length.

2. The apparatus of claim 1 further comprising a pumping element that accelerates the blood and delivers the blood from the blood inlet to the central void.

3. The apparatus of claim 2 wherein the pumping element comprises a plurality of vanes.

4. The apparatus of claim 1 wherein the inner member has at least one vane attached thereto.

5. The apparatus of claim 1 further comprising a girdle disposed about an exterior surface of the fiber bundle.

6. The apparatus of claim 1 wherein the fiber bundle comprises multiple layers of a hollow fiber mat, and the apparatus further comprises an adhesive material interposed the multiple layers.

7. The apparatus of claim 1 further comprising a gas manifold coupled to the fiber bundle and a baffle plate disposed within the gas manifold and adapted to urge blood in the gas manifold that has leaked from the fiber bundle to exit the housing via the gas outlet.

8. The apparatus of claim 1, wherein the inner member is coupled to the fiber bundle.

9. The apparatus of claim 1 further comprising a port that communicates with the central void and adapted to permit venting of gas collected within the central void.

10. A method for processing blood comprising:
providing a device including a housing having a gas inlet, a gas outlet, a blood inlet, a blood outlet, a gas transfer element disposed for rotation within the housing, the gas transfer element having a first end, a second end, a central void, and an inner member disposed within the central void, the first end coupled to the gas inlet and the second end coupled to the gas outlet, the inner member having first and second inner member ends and being tapered from the first inner member end to the second inner member end;
flowing blood into the housing so that the blood enters the central void;
delivering a gas comprising oxygen to the gas transfer element so that at least oxygen is transferred to the blood passing through the device;
rotating the inner member to cause blood to flow outward from the central void into the gas transfer element; and
rotating the gas transfer element to oxygenate blood flowing through the housing.

11. The method of claim 10 wherein rotating the inner member comprises rotating the inner member at an angular velocity identical to an angular velocity of the gas transfer element.

12. The method of claim 10 wherein providing a device comprises providing a device wherein the gas transfer element has a plurality of fibers and means for reducing outward bowing of the fibers.

13. The method of claim 10 further comprising venting gas that collects within in the central void.

14. A method for processing blood comprising:
providing a device including a housing having a gas inlet, a gas outlet, a blood inlet, a blood outlet, a gas transfer element disposed for rotation within the housing, the gas transfer element having a first end, a second end, a central void, the first end coupled to the gas inlet and the second end coupled to the gas outlet, and a pumping element positioned to receive the blood from the blood inlet prior to entry into the central void;
flowing blood into the housing so that the blood enters the pumping element;
rotating the pumping element to accelerate and deliver the blood into the central void;
delivering a gas comprising oxygen to the gas transfer element so that at least oxygen is transferred to the blood passing through the device;

rotating the gas transfer element to cause blood to flow outward from the central void into the gas transfer element and oxygenate blood flowing through the housing.

15. The method of claim 14 wherein providing a device comprises providing a device having an inner member rotatably disposed within the central void.

16. The method of claim 15 wherein providing a device having an inner member comprises providing a device having an inner member having first and second ends, the inner member being tapered from the first end to the second end.

17. The method of claim 15 further comprising rotating the inner member at an angular velocity identical to an angular velocity of the gas transfer element.

18. The method of claim 14 further comprising controlling the rates of rotation of the gas transfer element and the pumping element.

19. The method of claim 14 wherein providing a device comprises providing a device wherein the gas transfer element has a plurality of fibers and means for reducing outward bowing of the fibers.

20. The method of claim 14 further comprising venting gas that collects within in the central void.

21. A system for processing blood comprising:
a housing having a gas inlet, a gas outlet, a blood inlet and a blood outlet;
a fiber bundle disposed for rotation within the housing, the fiber bundle having a central void in fluid communication with the blood inlet;
a girdle disposed about an exterior surface of the fiber bundle; and
an inner member disposed within the central void, the inner member being rotatable relative to the housing.

22. The apparatus of claim 21 further comprising a pumping element that accelerates the blood and delivers the blood from the blood inlet to the central void.

23. The apparatus of claim 22 wherein the pumping element comprises a plurality of vanes.

24. The apparatus of claim 21 wherein the inner member has at least one vane attached thereto.

25. The apparatus of claim 21 wherein the inner member has a length and is tapered along the length.

26. The apparatus of claim 21 wherein the fiber bundle comprises multiple layers of a hollow fiber mat, and the apparatus further comprises an adhesive material interposed the multiple layers.

27. The apparatus of claim 21 further comprising a gas manifold coupled to the fiber bundle and a baffle plate disposed within the gas manifold and adapted to urge blood in the gas manifold that has leaked from the fiber bundle to exit the housing via the gas outlet.

28. The apparatus of claim 21, wherein the inner member is coupled to the fiber bundle.

29. The apparatus of claim 21 further comprising a port that communicates with the central void and adapted to permit venting of gas collected within the central void.

30. A system for processing blood comprising:
a housing having a gas inlet, a gas outlet, a blood inlet and a blood outlet;
a fiber bundle disposed for rotation within the housing, the fiber bundle having a central void in fluid communication with the blood inlet;
a gas manifold coupled to the fiber bundle;
a baffle plate disposed within the gas manifold and adapted to urge blood in the gas manifold that has leaked from the fiber bundle to exit the housing via the gas outlet; and
an inner member disposed within the central void, the inner member being rotatable relative to the housing.

31. The apparatus of claim 30 further comprising a pumping element that accelerates the blood and delivers the blood from the blood inlet to the central void.

32. The apparatus of claim 31 wherein the pumping element comprises a plurality of vanes.

33. The apparatus of claim 30 wherein the inner member has at least one vane attached thereto.

34. The apparatus of claim 30 wherein the inner member has a length and is tapered along the length.

35. The apparatus of claim 30 further comprising a girdle disposed about an exterior surface of the fiber bundle.

36. The apparatus of claim 30 wherein the fiber bundle comprises multiple layers of a hollow fiber mat, and the apparatus further comprises an adhesive material interposed the multiple layers.

37. The apparatus of claim 30, wherein the inner member is coupled to the fiber bundle.

38. The apparatus of claim 30 further comprising a port that communicates with the central void and adapted to permit venting of gas collected within the central void.

39. A method for processing blood comprising:
providing a device including a housing having a gas inlet, a gas outlet, a blood inlet, a blood outlet, a gas transfer element disposed for rotation within the housing, the gas transfer element having a first end, a second end, a plurality of fibers, means for reducing outward bowing of the fibers, a central void, and an inner member disposed within the central void, the first end coupled to the gas inlet and the second end coupled to the gas outlet;
flowing blood into the housing so that the blood enters the central void;
delivering a gas comprising oxygen to the gas transfer element so that at least oxygen is transferred to the blood passing through the device;
rotating the inner member to cause blood to flow outward from the central void into the gas transfer element; and
rotating the gas transfer element to oxygenate blood flowing through the housing.

40. The method of claim 39 wherein rotating the inner member comprises rotating the inner member at an angular velocity identical to an angular velocity of the gas transfer element.

41. The method of claim 39 wherein providing a device comprises providing a device wherein the inner member has first and second ends and is tapered from the first end to the second end.

42. The method of claim 38 further comprising venting gas that collects within in the central void.

* * * * *